United States Patent [19]
Wright, Jr.

[11] 3,984,562
[45] Oct. 5, 1976

[54] SUBSTITUTED BENZODIAZEPINES AND METHOD OF USE
[75] Inventor: William Blythe Wright, Jr., Woodcliff Lake, N.J.
[73] Assignee: American Cyanamid Company, Stamford, Conn.
[22] Filed: Feb. 24, 1975
[21] Appl. No.: 552,021

[52] U.S. Cl. .................. 424/274; 260/239 BD; 260/247.2 A; 260/268 TR; 260/293.61; 260/326.31; 424/248; 424/250; 424/267
[51] Int. Cl.² .................................. C07D 487/04
[58] Field of Search .............. 260/239 BD, 247.2 A, 260/268 TR, 293.61, 326.31; 424/248, 250, 267, 274

[56] References Cited
UNITED STATES PATENTS
3,763,183   10/1973   Carabateas .................. 260/326.3
3,891,626   6/1975    Okamoto et al. ............. 260/239 BB Primary Examiner—G. Thomas Todd
Attorney, Agent, or Firm—Denis A. Polyn

[57] ABSTRACT

Aminoacyl derivatives of 2,3,5,10,11,11a-hexahydro-1H-pyrrolo[2,1-c] [1,4]benzodiazepines in the form of their racemic mixtures, optical isomers and salts, their method of preparation and method of use are described. The compounds are useful in treating anxiety in warm-blooded animals.

11 Claims, No Drawings

SUBSTITUTED BENZODIAZEPINES AND METHOD OF USE

DESCRIPTION OF THE INVENTION

This invention relates to new racemic compounds, optical isomers, salts, methods of preparation and method of use of aminoacyl derivatives of 2,3,5,10,11,11a-hexahydro-1H-pyrrolo[2,1-c][1,4]benzodiazepines.

The compounds of the present invention may be illustrated by the following formula:

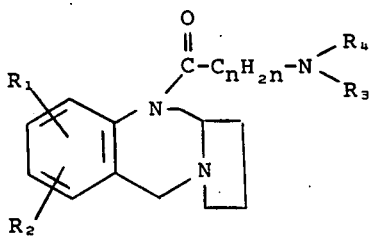

wherein $R_1$ and $R_2$ are selected from the group consisting of hydrogen, lower alkyl, halogen, nitro, amino, diloweralkylamino, trifluoromethyl, lower alkoxy, lower carboxylic acyl amino, lower carboxylic acyloxy, benzyloxy and hydroxy and $R_1$ and $R_2$ taken together on adjacent carbons may be methylenedioxy; $R_3$ and $R_4$ are selected from the group consisting of hydrogen, lower alkyl, allyl, propargyl, cycloalkylmethyl and benzyl and taken together with the nitrogen may be pyrrolidinyl, piperidino, 4-methylpiperidino, hexamethyleneimino, morpholino, 1-piperazinyl, 4-methyl-1-piperazinyl or 4-phenyl-1-piperazinyl and $n$ is 1–4.

The terms "lower alkyl," lower carboxylic acyl, lower carboxylic acyloxy and "lower alkoxy" include those having hydrocarbon groups of 1–4 carbon atoms. The term "cycloalkyl" includes those having 3–6 carbon atoms. The term halogen includes chlorine, fluorine and bromine.

The free bases of the racemic compounds or optical isomers of this invention, in general, may be either liquids or solids at room temperature. The free bases are, in general, relatively insoluble in water, but soluble in most organic solvents such as lower alkyl alcohols, benzene, acetone, chloroform or the like. These compounds form acid addition salts with strong acids, such as hydrochloric acid, sulfuric acid, phosphoric acid, and the like. The compounds also form salts with organic acids, as for example, tartaric, fumaric and maleic acids. These salts, in general, are soluble in water, methanol and ethanol but relatively insoluble in benzene, ether, petroleum ether and the like.

The compounds of this invention can be prepared by one of the following methods, of which the first method has been found most advantageous.

In the first method a derivative of 2,3,5,10,11,11a-hexahydro-1H-pyrrolo[2,1-c][1,4]benzodiazepine is treated with a haloacyl halide (or anhydride) and then with an amine and the desired 10-aminoacyl-2,3,5,10,11,11a-hexahydro-1H-pyrrolo[2,1-c][1,4]benzodiazepine is recovered from the reaction mixture. The following equations describe these reactions:

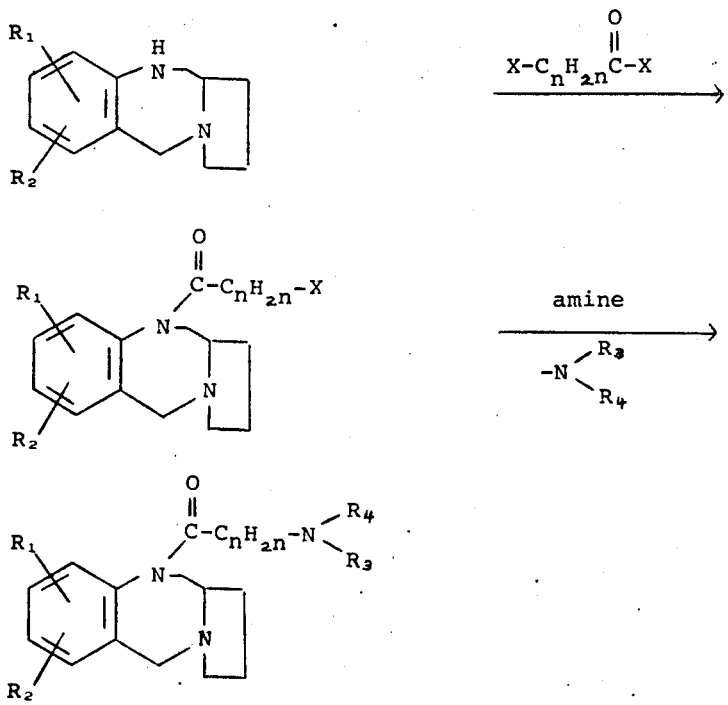

wherein X is halogen, $R_1$ and $R_2$ are hydrogen, lower alkyl, halogen, nitro, diloweralkylamino, trifluoromethyl, lower alkoxy or benzyloxy and $R_1$ and $R_2$ taken together on adjacent carbons may be methylenedioxy and $R_3$ and $R_4$ are as previously described. When $R_1$ or $R_2$ are amino, the compound is prepared by reduction (catalytic reduction is preferred) of the corresponding nitro derivative and when $R_1$ or $R_2$ are hydroxy, the product is best obtained by catalytic reduction of the corresponding benzyloxy derivative. The lower carboxylicacylamine and lower carboxylicacyloxy compounds are best prepared by acylation of the corresponding amino and hydroxy derivatives.

The reactions are usually carried out at room temperature or at reflux temperature in a suitable inert solvent such as benzene, chloroform or tetrahydrofuran.

The 2,3,5,10,11,11a-hexahydro-1H-pyrrolo[2,1-c][1,4]benzodiazepines used as intermediates may be prepared by several methods previously described in the literature. For example, 1,2,3,11a-tetrahydro-5H-pyrrolo[2,1-c][1,4]benzodiazepin-5,11-(10H) diones can be prepared by treating substituted isatoic acids with proline (A. Ermili and G. Filacchioni, Ann. Chim. (Rome) 59, 770–786 (1969); P. M. Carabateas, U.S. Pat. No. 3,732,212, May 8, 1973) and then reduced with lithium aluminum hydride, borane or the like. Also, 1,2,3,5,10,11a-hexahydro-1H-pyrrolo[2,1-c][1,4]benzodiazepin-11-ones can be prepared from nitrobenzyl halides and proline or proline esters as described in my copending application Ser. No. 494,657, filed Aug. 5, 1974. These compounds can also be reduced by lithium aluminum hydride or borane to the desired 2,3,5,10,11,11a-hexahydro-1H-pyrrolo[2,1-c][1,4]benzodiazepines.

In the second method, a derivative of 2,3,5,10,11,11a-hyexahydro-1H-pyrrolo[2,1-c][1,4]benzodiazepine is treated with an aminoacyl halide (or anhydride) and the desired product is recovered from the reaction mixture. This may be represented schematically as follows:

doses producing anxiolytic activity and toxic symptoms.

The anti-anxiety properties of these compounds have been established in a test which indicates anxiolytic activity by a measure of protection from convulsions resulting from the administration of pentylenetetrazole. Graded dose levels of the compounds are administered orally, in a 2% starch vehicle, to groups of at least 5 rats. At the estimated time of peak effect, the rats are treated intravenously with pentylenetetrazole at a dose of 21 to 23 mg./kg. of body weight. This dose is estimated to cause clonic seizures in 99% of unprotected rats. The effective dose of the test compound for protection of 50% of the animals ($ED_{50}$) is calculated by the method of D. H. Finney in Statistical Methods in Biological Assay, Second Edition, Hafner Publishing Co., New York, 1964, pp. 456–457. The results of this test on representative compounds of the present invention are given in the following table in comparison with meprobromate which is tested in the same manner. It has been reported [R. T. Hill and D. H. Tedeschi, "Animal Testing and Screening Procedures in Evaluating Psychotropic Drugs" in An Introduction to Psychopharmacology, Eds. R. R. Rech and K. E. Moore, Raven Press, New York, pp. 237–288 (1971)] that there is a high degree of correlation between antagonism of pentylenetetrazole seizures in rats and anti-anxiety effects in higher warm-blooded animals.

TABLE

| Compound | Median Effective Oral Dose (mg./kg.) $ED_{50}$ |
|---|---|
| (−)-7-chloro-2,3,5,10,11,11a-hexahydro-10-[3-(1-pyrrolidinyl)propionyl]-1H-pyrrolo[2,1-c][1,4]benzodiazepine ditartrate dihydrate | 7 |
| (−)-2,3,5,10,11,11a-hexahydro-10-(3-piperidinopropionyl)-1H-pyrrolo[2,1-c][1,4]-benzodiazepine ditartrate dihydrate | 16 |
| (−)-2,3,5,10,11,11a-hexahydro-10-[3-(1-pyrrolidinyl)propionyl]-1H-pyrrolo-[2,1-c][1,4]benzodiazepine ditartrate dihydrate | 57 |
| meprobromate | 22 |

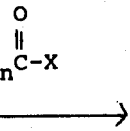

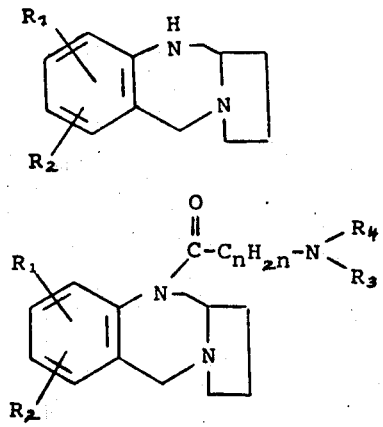

wherein $R_1$, $R_2$, $R_3$, $R_4$, $n$ and X are as described above with the same exceptions.

In carrying out the preparation of the compounds of this invention, combinations of the above methods may be used.

The compounds of the present invention possess central nervous system activity at non-toxic doses, and as such, are useful as anxiolytic agents. The compounds have been tested pharmacologically and found to have properties which show a desirable wide spread between The compounds of the present invention may be administered to warm-blooded animals, in either their racemic or optical isomeric forms, orally, or parenterally if desired, and when so administered, may be considered as tranquilizing agents for therapeutically desirable treatment of anxiety in warm-blooded animals. The dosage regimen can be adjusted to provide optimum therapeutic response. Thus, for example, several doses may be administered daily, or the dose may be reduced proportionately as indicated by the requirements of the particular therapeutic situation.

For therapeutic administration the compounds of this invention may be incorporated with pharmaceutical carriers such as excipients and used, for example, in the form of tablets, dragees, capsules, liquids, elixirs, emulsions, suspensions, syrups, chocolate candy, wafers, chewing gum or the like for oral administration.

Parenteral solutions and suspensions may be prepared for intramuscular or subcutaneous administration, and suppositories may be prepared for rectal administration. Such compositions and preparations should contain at least 0.1% of active component. The percentage of the compositions and preparations may, of course, be varied, and may conveniently be between 2% and 60% or more of the weight of the unit. The amount of active component in such therapeutically useful compositions or preparations is such that a suitable dosage of from about 1.0 to about 25.0 mg/kg/day will be obtained. Preferred compositions or preparations according to the present invention are prepared so that a dosage unit form contains between about 20 and about 400 mg of the therapeutically active component.

The compounds of this invention are physiologically active as anxiolytic agents As such they can be incorporated in various pharmaceutical forms such as set forth immediately above, for immediate or sustained release, by combining with suitable pharmaceutical carriers. They may be in the form of a single therapeutic dose or in small units for multiple dosages or in large units for division into single doses. Obviously, in addition to the therapeutic tranquilizing compound there may be present excipients, binders, fillers, and other therapeutically inert ingredients necessary in the formulation of the desired pharmaceutical preparation.

The following specific examples illustrate the preparation of the racemic compounds and optical isomers of the present invention.

EXAMPLE 1

Preparation of
(−)-7-Chloro-2,3,5,10,11,11a-hexahydro-10-[3-(1-pyrrolidinyl)-propionyl]-1H-pyrrolo[2,1-c][1,4]benzodiazepine A mixture of 8.9 g of (−)-7-chloro-2,3,5,10,11,11a-hexahydro-1H-pyrrolo[2,1-c][1,4]benzodiazepine (prepared as described in U.S. Pat. No. 3,732,212), 150 ml. of benzene and 8 ml. of 3-chloropropionyl chloride is heated at reflux temperature for 3 hours, cooled and then stirred with 200 ml. of water and 50 ml. of 5N sodium hydroxide. The layers are separated and the aqueous layer is extracted with benzene. The combined benzene layers are washed twice with water, dried over magnesium sulfate and concentrated to about 100 ml. This solution contains (−) -7-chloro-10-(3-chloropropionyl)-2,3,5,10,11,11a-hexahydro-1H-pyrrolo[2,1-c][1,4]benzodiazepine. The hydrochloride salt melts at 215°–217°C., $[\alpha]_D^{25}$ −110° (methanol).

The above solution and 20 ml. of pyrrolidine are heated at reflux temperature for 5 hours, cooled and shaken with potassium carbonate solution. The benzene layer is separated, washed three times with water, dried over magnesium sulfate and concentrated to remove the solvent. The residue, (−)-7-chloro-2,3,5,10,11,11a-hexahydro-10-[3-(1-pyrrolidinyl)propionyl]-1H-pyrrolo[2,1-c][1,4]benzodiazepine, is a viscous oil, $[\alpha]_D^{25}$ − 84.9° (methanol).

The above oil is dissolved in ether and treated with 0.2M tartaric acid in acetone. The resulting white precipitate is filtered, washed with ether, and dried under reduced pressure at 40°C. giving the ditartrate dihydrate salt which has an indefinite melting point, $[\alpha]_D^{25}$ −32.4° (methanol). Anal. calcd. for $C_{27}H_{42}ClN_3O_{15}$: C, 47.4; H, 6.2; Cl, 5.2; N, 6.1. Found: C, 47.5; H, 5.8; Cl, 4.9; N, 6.1.

EXAMPLE 2

Preparation of
(−)-2,3,5,10,11,11a-Hexahydro-10-[3-(1-pyrrolidinyl)-propionyl]-1H-pyrrolo[2,1-c][1,4]benzodiazepine A mixture of 9.4 g. of (−) -2,3,5,10,11,11a-hexahydro-1H-pyrrolo[2,1-c][1,4]benzodiazepine (prepared as described in U.S. Pat. No. 3,732,212), 150 ml. of benzene and 10 ml. of 3-chloropropionyl chloride is heated on a steam bath for 3 hours, cooled and then stirred with 200 ml. of water and 50 ml. of 5N sodium hydroxide. The layers are separated and the aqueous layer is extracted with benzene. The combined benzene layers are washed twice with water, dried over magnesium sulfate and concentrated to about 100 ml. This solution contains (−)-10-chloropropionyl-2,3,5,10,11,11a-hexahydro-1H-pyrrolo[2,1-c][1,4]benzodiazepine.

The above benzene solution and 20 ml. of pyrrolidine are heated at reflux temperature for 5 hours, cooled and stirred with sodium carbonate solution. The layers are separated and the benzene layer is washed three times with water, dried over magnesium sulfate and concentrated to remove the solvent. The residue (−)-2,3,5,10,11,11a-hexahydro-10-[3-(1-pyrrolidinyl)propionyl]-1H-pyrrolo[2,1-c](1,4)benzodiazepine, is a viscous oil.

The ditartrate dihydrate salt (prepared as described in Example 1) has an indefinite melting point, $[\alpha]_D^{25}$ −42°, (methanol). Anal. calcd for $C_{27}H_{43}N_3O_{15}$ : C, 49.9; H, 6.68; N, 6.43; $H_2O$, 5.5, Found: C, 49.9; H, 6.46; N, 6.19; $H_2O$, 5.7.

EXAMPLE 3

Preparation of
(−)-2,3,5,10,11,11a-Hexahydro-10-(3-piperidinopropionyl)-1H-pyrrolo[2,1-c][1,4]benzodiazepine A mixture of 20 ml. of piperidine and about 100 ml. of a benzene solution of (−)-10-chloropropionyl-2,3,5,10,11,11a-hexahydro-1H-pyrrolo[2,1-c][1,4]benzodiazepine (prepared as described in Example 2) is heated at reflux temperature for 5 hours, cooled and stirred with sodium carbonate solution. The layers are separated, and the benzene layer is washed three times with water, dried over magnesium sulfate and concentrated to remove the solvent. The residue, (−)-2,3,5,10,11,11a-hexahydro-10-(3-piperidinopropionyl)-1H-pyrrolo[2,1-c][1,4]benzodiazepine, is a viscous oil.

The ditartrate dihydrate salt (prepared as described in Example 1) has an indefinite melting point, $[\alpha]_D^{25}$ − 45° (methanol).

EXAMPLE 4

Preparation of
(+)-7-Chloro-2,3,5,10,11,11a-hexahydro-10-[3-(1-pyrrolidinyl)propionyl-1H-pyrrolo[2,1-c][1,4]benzodiazepine The above compound is obtained when (+)-7-chloro-2,3,5,10,11,11a-hexahydro-1H-pyrrolo[2,1-c][1,4]benzodiazepine is treated with 3-chloropropionyl chloride and pyrrolidine by the procedure of Example 1.

EXAMPLE 5

Preparation of
(+)-7-Chloro-2,3,5,10,11,11a-hexahydro-10-[3-(1-pyrrolidinyl)propionyl-1H-pyrrolo[2,1-c][1,4]benzodiazepine When (±)-7-Chloro-2,3,5,10,11,11a-hexahydro-1H-pyrrolo[2,1-C][1,4] benzodiazepine is treated with 3-chloropropionyl chloride and pyrrolidine by the procedure of Example 1, the above compound is obtained.

EXAMPLE 6

Preparation of
(−)-7-Chloro-2,3,5,10,11,11a-hexahydro-10-(3-morpholinopropionyl)-1H-pyrrolo[2,1-c[[1,4]benzodiazepine This compound is obtained when morpholine is substituted for pyrrolidine in the procedure of Example 1. The ditartrate dihydrate salt precipitates in white crystals, $[\alpha]_D^{25}$ −32° (methanol).

EXAMPLE 7

Preparation of
(−)-7-Chloro-2,3,5,10,11,11a-hexahydro-10-[3-(4-methyl-1-piperazinyl)propionyl]-1H-pyrrolo[2,1-c][1,4]-benzodiazepine The above compound is obtained when 1-methylpiperazine is substituted for pyrrolidine in the procedure of Example 1. The trimaleate salt melts at 159°–161°C., $[\alpha]_D^{25}$ −59.3°(methanol).

EXAMPLE 8

Preparation of
(−)-2,3,5,10,11,11-a-Hexahydro-10-(3-piperazinyl propionyl)-1H-pyrrolo[2,1-c][1,4]benzodiazepine If piperazine is substituted for pyrrolidine in the procedure of Example 2, the above compound is obtained.

EXAMPLE 9

Preparation of
(−)-7-Chloro-2,3,5,10,11,11-a-Hexahydro-10-[3-(4-phenyl-1-piperazinyl)propionyl]-1H-pyrrolo[2,1-c][1,4]benzodiazepine This compound is obtained when phenylpiperazine is substituted for pyrrolidine in the procedure of Example 1.

EXAMPLE 10

Preparation of
(−)-7-Chloro-2,3,5,10,11,11a-hexahydro-10-[3-(3-methylpiperidino)propionyl]-1H-pyrrolo[2,1-c][1,4]benzodiazepine If 3-methylpiperidine is substituted for pyrrolidine in the procedure of Example 1, the above compound is obtained.

EXAMPLE 11

Preparation of
(−)-7-Chloro-2,3,5,10,11,11a-hexahydro-10-[3-(allylmethylamino)propionyl]-1H-pyrrolo[2,1-c][1,4]benzodiazepine The above compound is obtained when allylmethylamine is substituted for pyrrolidine in the procedure of Example 1.

EXAMPLE 12

Preparation of
(−)-7-Chloro-10-(3-dipropylaminopropionyl)-2,3,5,10,11,11-a-hexahydro-1H-pyrrolo[2,1-c][1,4]benzodiazepine This compound is obtained when dipropylamine is substituted for pyrrolidine in the procedure of Example 1. The ditartrate dihydrate salt is obtained as white crystals, $[\alpha]_D^{25}$ −35° (methanol).

13

Preparation of
10-3-Benzylmethylamino)propionyl-7-chloro-2,3,5,10,11,11a-hexahydro-1H-pyrrolo[2,1-c][1,4]benzodiazepine This compound is obtained when 7-chloro-2,3,5,10,11,11a-hexahydro-1H-pyrrolo[2,1-c][1,4]benzodiazepine is treated with 3-chloropropionyl chloride and benzylmethylamine by the procedure of Example 1.

EXAMPLE 14

Preparation of
10-(3-Cyclobutylmethylaminopropionyl)-7-chloro-2,3,5,10,11,11-a-hexahydro-1H-pyrrolo[2,1-c][1,4]benzodiazepine When 7-chloro-2,3,5,10,11,11-a-hexahydro-1-H-pyrrolo[2,1-c][1,4]benzodiazepine is treated with 3-chloropropionyl chloride and cyclobutylmethylamine by the procedure of Example 1, the above compound is obtained.

EXAMPLE 15

Preparation of
10-(3-Butylaminopropionyl)-7-chloro-2,3,5,10,11,11a-hexahydro-1H-pyrrolo[2,1-c][1,4]benzodiazepine The above compound is obtained when 7-chloro-2,3,5,10,11,11a-hexahydro-1H-pyrrolo[2,1-c][1,4]benzodiazepine is treated with 3-chloropropionyl chloride and butylamine by the procedure of Example 1.

EXAMPLE 16

Preparation of
7-Chloro-2,3,5,10,11,11a-hexahydro-10-[(1-pyrrolidinyl)acetyl]-1H-pyrrolo[2,1-c][1,4]benzodiazepine When chloroacetyl chloride is substituted for 3-chloropropionyl chloride in the procedure of Example 1, the above compound is obtained.

EXAMPLE 17

Preparation of
7-Chloro-2,3,5,10,11,11a-hexahydro-10-[4-(1-pyrrolidinyl)butyryl-1H-pyrrolo[2,1-c][1,4]benzodiazepine This compound is obtained when 4-bromobutyryl bromide is substituted for 3-chloropropionyl chloride in the procedure of Example 1.

EXAMPLE 18

Preparation of
7-Chloro-2,3,5,10,11,11a-hexahydro-10-[5-(1-pyrrolidinyl)valeryl]-1H-pyrrolo[2,1-c][1,4]benzodiazepine If 5-bromovaleryl bromide is substituted for 3-chloropropionyl chloride in the procedure of Example 1. The above compound is obtained.

EXAMPLE 19

Preparation of
(−)-7-Chloro-10-(3-dimethylaminopropionyl-2,3,5,10,11,11a-hexahydro-1H-pyrrolo[2,1-c][1,4]benzodiazepine This compound is obtained when dimethylamine is substituted for pyrrolidine in the procedure of Example 1. A ditartrate dihydrate salt is obtained as white crystals, $[\alpha]_D^{25}$ −34° (methanol).

EXAMPLE 20

Preparation of
(−)-7-Chloro-2,3,5,10,11,11a-hexahydro-10-(3-hexamethyleneiminopropionyl)-1H-pyrrolo[2,1-c][1,4]benzodiazepine When hexamethyleneimine is substituted for pyrrolidine in the procedure of Example 1, the above compound is obtained. The ditartrate monohydrate salt is obtained, $[\alpha]_D^{25}$ −26° (methanol).

EXAMPLE 21

Preparation of
(−)-2,3,5,10,11,11a-Hexahydro-10-(3-morpholinopropionyl)-1H-pyrrolo[2,1-c][1,4-]benzodiazepine The above compound is obtained when morpholine is substituted for pyrrolidine in the procedure of Example 2. The ditartrate monohydrate salt is obtained as white crystals, $[\alpha]_D^{25}$ −44° (methanol).

EXAMPLE 22

Preparation of
(−)-2,3,5,10,11,11a-Hexahydro-10-(3-piperidinopropionyl)-1H-pyrrolo[2,1-c][1,4]benzodiazepine If piperidine is substituted for pyrrolidine in the procedure of Example 2, this compound is obtained. The ditartrate monohydrate salt, $[\alpha]_D^{25}$ −41° (methanol) is obtained as white crystals.

EXAMPLE 23

Preparation of
(−)-8-Chloro-2,3,5,10,11,11a-hexahydro-10-[3-(1-pyrrolidinyl)propionyl]-1H-pyrrolo[2,1-c][1,4]benzodiazepine A mixture of 56 g. of 4-chloroisatoic anhydride, 37 g. of L-proline and 200 ml. of dimethylsulfoxide is heated on the steam bath for 3 hours, cooled and diluted, while stirring with 400 ml. of water. The crystals which separate are filtered off and recrystallized from ethanol. The (+)-8-chloro-1,2,3,11a-tetrahydro-5H-pyrrolo[2,1-c][1,4]benzodiazepine-5,11(10H)dione melts at 299°–301°C., $[\alpha]_D^{25}$ +610° (DMF).

A mixture of 29.2 g. of the above compound and 300 ml. of tetrahydrofuran is stirred under nitrogen and 250 ml. of a 1.0M solution of lithium aluminum hydride in tetrahydrofuran is added. The mixture is stirred at room temperature for 1 hour, heated on the steam bath for 2 hours, and then decomposed by the addition of 9.5 ml. water. 9.5 ml. of 15% sodium hydroxide and 28.5 ml. water. The precipitate is filtered off and washed with tetrahydrofuran and the mother liquor is concentrated to remove the solvent. The residue is recrystallized from ethyl acetate. The (−)-8-chloro-2,3,5,10,11,11a-hexahydro-1H-pyrrolo[2,1-c][1,4]benzodiazepine melts at 131°–133°C., $[\alpha]_D^{27}$ −237° (methanol).

A mixture of 10.5 g. of the above compound, 130 ml. of benzene and 9 ml. of 3-chloropropionyl chloride is heated on the steam bath for 3 hours, cooled, concentrated and the residue dissolved in chloroform and shaken with 260 ml. of 1N sodium hydroxide. The layers are separated and the chloroform layer is washed twice with water and concentrated to obtain the 8-chloro-10-(3-chloropropionyl)-2,3,5,10,11,11a-hexahydro-1H-pyrrolo[2,1-c][1,4]benzodiazepine as an oil.

The oil is redissolved in chloroform, 30 ml. of pyrrolidine are added and the solution is heated at reflux temperature for 3 hours and cooled. The solution is washed with a solution of 9 g. potassium carbonate in 150 ml. of water and then three times with water, dried over magnesium sulfate and concentrated to recover the (−)-8-chloro-2,3,5,10,11,11a-hexahydro-10-[3-(1-pyrrolidinyl)propionyl]-1H-pyrrolo[2,1-c][1,4]benzodiazepine. This material is dissolved in ethanol and two molar equivalents of 0.2M tartaric acid in ethanol are added. Ether is added and the precipitate is filtered off, washed with ether and dried in a vacuum oven. The ditartrate hemihydrate salt has an indefinite melting point, $[\alpha]_D^{25}$ −21° (methanol). If desired, the crystals may be recrystallized from ethanol and ether.

EXAMPLE 24

Preparation of
(−)-8-Chloro-2,3,5,10,11,11a-hexahydro-10-(3-piperidinopropionyl)-1H-pyrrolo[2,1-c][1,4]benzodiazepine The above compound is obtained when piperidine is substituted for pyrrolidine in the procedure of Example 23.

EXAMPLE 25

Preparation of
(−)-2,3,5,10,11,11a-Hexahydro-7-methyl-10-[3-(1-pyrrolidinyl)propionyl]-1H-pyrrolo[2,1-c][1,4]benzodiazepine When 5-methylisatoic anhydride, m.p. 252°–255°C., is substituted for 4-chloroisatoic anhydride in the procedure of Example 23, the above compound is obtained. The ditartrate hemihydrate has an indefinite melting point, $[\alpha]_D^{25}$ −33° (methanol).

EXAMPLE 26

Preparation of
(−)-7-Benzyloxy-2,3,5,10,11,11a-hexahydro-10-[3-(1-pyrrolidinyl)propionyl]-1H-pyrrolo[2,1-c][1,4]benzodiazepine This compound is obtained when 5-benzyloxyisatoic anhydride is substituted for 4-chloroisatoic anhydride in the procedure of Example 23.

EXAMPLE 27

Preparation of
(−)-2,3,5,10,11,11a-Hexahydro-7-methoxy-10-[3-(1-pyrrolidinyl)propionyl]-1H-pyrrolo[2,1-c][1,4]benzodiazepine When 5-methoxyisatoic anhydride is substituted for 4-chloroisatoic anhydride, in the procedure of Example 23, the above compound is obtained.

EXAMPLE 28

Preparation of
(−)-7-Butoxy-2,3,5,10,11,11a-hexahydro-10-[3-(1-pyrrolidinyl)propionyl]-1H-pyrrolo[2,1-c][1,4]benzodiazepine If 5-butoxyisatoic anhydride is substituted for 4-chloroisatoic anhydride in the procedure of Example 23, this compound is obtained.

EXAMPLE 29

Preparation of
(−)-2,3,5,10,11,11a-Hexahydro-7,8-methylenedioxy-10-[3-(1-pyrrolidinyl)propionyl]-1H-pyrrolo[2,1-c][1,4]benzodiazepine When 4,5-methylenedioxy isatoic anhydride is substituted for 4-chloroisatoic anhydride in the procedure of Example 23, the above compound is obtained.

EXAMPLE 30

Preparation of
(−)-2,3,5,10,11,11a-Hexahydro-7-trifluoromethyl-10-[3-(1-pyrrolidinyl)propionyl]-1H-pyrrolo[2,1-c][1,4]benzodiazepine This compound is obtained when 5-trifluoromethylisatoic anhydride is substituted for 4-chloroisatoic anhydride in the procedure of Example 23.

EXAMPLE 31

Preparation of
(−)-8,9-Dimethyl-2,3,5,10,11,11a-hexahydro-10-[3-(1-pyrrolidinyl)propionyl]-1H-pyrrolo[2,1-c][1,4]benzodiazepine If 3,4-dimethylisatoic anhydride, m.p. 293°–294°C., is substituted for 4-chloroisatoic anhydride in the procedure of Example 23, the above compound is obtained.

EXAMPLE 32

Preparation of
(−)-6,9-Dimethyl-2,3,5,10,11,11a-hexahydro-10-[3-(1-pyrrolidinyl)propionyl]-1H-pyrrolo[2,1-c][1,4]benzodiazepine The above compound is obtained when 3,6-dimethylisatoic anhydride, m.p. 295°–298°C., is substituted for 4-chloroisatoic anhydride in the procedure of Example 23.

EXAMPLE 33

Preparation of
(−)-7,9-Dichloro-2,3,5,10,11,11a-hexahydro-10-[3-(1-pyrrolidinyl)propionyl]-1H-pyrrolo[2,1-c][1,4]benzodiazepine When 3,5-dichloroisatoic anhydride is substituted for 4-chloroisatoic anhydride in the procedure of Example 23, the above compound is obtained.

EXAMPLE 34

Preparation of
2,3,5,10,11,11a-Hexahydro-7-nitro-10-[3-(1-pyrrolidinyl)propionyl]-1H-pyrrolo[2,1-c][1,4]benzodiazepine A mixture of 26.1 g. 7-nitro-1,2,3,11a-tetrahydro-5H-pyrrolo[2,1-c] [1,4]benzodiazepin-5,11(10H)-dione, m.p. 249°–251°C., (prepared from 5-nitroisatoic acid and proline) and 250 ml. of tetrahydrofuran is cooled under nitrogen and 300 ml. of 1M borane in tetrahydrofuran is added. The mixture is heated on the steam bath for 5 hours, cooled and 95 ml. of 6N hydrochloric acid is added. The solvent is distilled off and 400 ml. of water and 70 g. of sodium hydroxide pellets are carefully added with cooling. The mixture is extracted with benzene and the benzene layer is washed with water and concentrated to obtain the 2,3,5,10,11,11a-hexahydro-7-nitro-1H-pyrrolo[2,1-c][1,4]benzodiazepine.

When the above compound is substituted for (−)-7-chloro-2,3,5,10,11,11a-hexahydro-1H-pyrrolo[2,1-c][1,4]benzodiazepine in the procedure of Example 1, 2,3,5,10,11,11a-hexahydro-7-nitro-10-[3-(1-pyrrolidinyl)propionyl]-1H-pyrrolo[2,1-c][1,4]benzodiazepine is obtained.

EXAMPLE 35

Preparation of
7-Amino-2,3,5,10,11,11a-hexahydro-10-[3-(1-pyrrolidinyl)propionyl]-1H-pyrrolo[2,1-c][1,4]-benzodiazepine A mixture of 5 g. of 2,3,5,10,11,11a-hexahydro-7-nitro-10-[3-(1-pyrrolidinyl)propionyl]-1H-pyrrolo[2,1-c][1,4]benzodiazepine, 250 ml. of ethanol and 2 g. of 10% palladium on carbon catalyst is shaken under about 3 atmospheres of hydrogen pressure in a Parr hydrogenerator until hydrogen uptake is complete. The catalyst is filtered off and the mother liquor is concentrated to obtain the 7-amino-2,3,5,10,11,11a-hexahydro-10-[3-(1-pyrrolidinyl)propionyl]-1H-pyrrolo[2,1-c] [1,4]benzodiazepine.

EXAMPLE 36

Preparation of 2,3,5,10,11,11a-Hexahydro-7-hydroxy-10-[3-(1-pyrrolidinyl)propionyl]-1H-pyrrolo[2,1-c][1,4]benzodiazepine A mixture of 5 g. of 7-benzoyloxy-2,3,5,10,11,11a-hexahydro-10-[3-(1-pyrrolidinyl)propionyl]-1H-pyrrolo[2,1-c] [1,4]benzodiazepine, 250 ml. of ethanol and 2 g. of 10% palladium-on-carbon catalyst is shaken in a Parr hydrogenator under about 3 atmospheres of hydrogen pressure until hydrogen uptake is complete. The catalyst is filtered off and the mother liquor is concentrated and 2,3,5,10,11,11a-hexahydro-7-hydroxy-10-[3-(1-pyrrolidinyl)propionyl]-1H-pyrrolo[2,1-c][1,4]benzodiazepine is obtained.

EXAMPLE 37

Preparation of 2,3,5,10,11,11a-Hexahydro-7-propionamide-10-[3-(1-pyrrolidinyl)propionyl]-1H-pyrrolo[2,1-c][1,4]benzodiazepine A solution of 10 g. of propionyl chloride in 20 ml. of benzene is added to a solution of 10 g. of 7-amino-2,3,5,10,11,11a-hexahydro-10-[3-(1-pyrrolidinyl)propionyl]-1H-pyrrolo[2,1-c][1,4]benzodiazepine in 100 ml. of benzene. The mixture is stirred for 30°C. for 48 hours, 50 ml. of saturated aqueous potassium carbonate solution are added, and the mixture is stirred for 30 minutes longer. The layers are separated, and the benzene layer is washed twice with water, dried over magnesium sulfate and concentrated. The residue contains 2,3,5,10,11,11a-hexahydro-7-propionamide-10-[3-(1-pyrrolidinyl)propionyl]-1H-pyrrolo[2,1-c][1,4]benzodiazepine, which can be further purified by partition chromatography using a hexane-methanol-celite system.

EXAMPLE 38

Preparation of 2,3,5,10,11,11a-Hexahydro-7-propionoxy-10-[3-(1-pyrrolidinyl)propionyl]-1H-pyrrolo[2,1-c][1,4]benzodiazepine The above compound is obtained when 2,3,5,10,11,11a-hexahydro-7-hydroxy-10-[3-(1-pyrrolidinyl)propionyl]-1H-pyrrolo[2,1-c] [1,4]benzodiazepine is treated with propionyl chloride by the procedure of Example 37.

EXAMPLE 39

Preparation of (−)-7-Chloro-2,3,5,10,11,11a-hexahydro-10-[3-(1-pyrrolidinyl)propionyl]-1H-pyrrolo-[2,1-c][1,4]benzodiazepine A mixture of 11.0 g. of (−)-7-chloro-2,3,5,10,11,11a-hexahydro-1H-pyrrolo[2,1-c][1,4]benzodiazepine and 150 ml. of benzene is stirred and 10.6 g. of 3-(1-pyrroliidinyl)propionyl chloride is added. The reaction mixture is heated on the steam bath for 2 hours, cooled and shaken with 1N sodium hydroxide. The layers are separated and the benzene is washed twice with water, dried over magnesium sulfate and concentrated. The residue contains (−)-7-chloro-2,3,5,10,11,11a-hexahydro-10-[3-(1-pyrrolidinyl)-propionyl]-1H-pyrrolo[2,1-c] [1,4]benzodiazepine, which can be further purified by partition chromatography on a heptane/methanol/celite system.

I claim:

1. A compound selected from those of the formula:

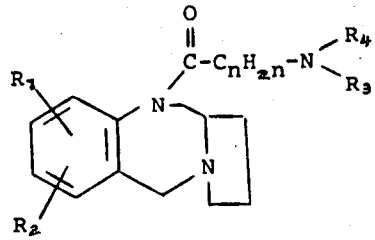

wherein $R_1$ and $R_2$ are selected from the group consisting of hydrogen, lower alkyl, halogen, nitro, amino, diloweralkylamino, trifluoromethyl, lower alkoxy, lower carboxylic acyloxy, benzyloxy and hydroxy and $R_1$ and $R_2$ taken together on adjacent carbons may be methylenedioxy; $R_3$ and $R_4$ are selected from the group consisting of hydrogen, lower alkyl, allyl, propargyl, $C_3$–$C_6$ cycloalkylmethyl and benzyl and taken together with the nitrogen may be pyrrolidinyl, piperidino, 4-methylpiperidino, hexamethyleneimino, morpholino, 1-piperazinyl, 4-methyl-1-piperazinyl or 4-phenyl-1-piperazinyl and $n$ is 1–4.

2. The compound in accordance with claim 1, (−)-7-chloro-2,3,5,10,11,11a-hexahydro-10-[3-(1-pyrrolidinyl)propionyl]-1H-pyrrolo[2,1-c][1,4]benzodiazepine.

3. The compound in accordance with claim 1, (−)-2,3,5,10,11,11a-hexahydro-10-[3-(1-pyrrolidinyl)propionyl]-1H-pyrrolo[2,1-c][1,4]benzodiazepine.

4. The compound in accordance with claim 1, (−)-2,3,5,10,11,11a-hexahydro-10-(3-piperidinopropionyl)-1H-pyrrolo[2,1-c] [1,4]benzodiazepine.

5. The compound in accordance with claim 1, (+)-7-chloro-2,3,5,10,11,11a-hexahydro-10-[3-(1-pyrrolidinyl)propionyl]-1H-pyrrolo[2,1-c][1,4]benzodiazepine.

6. The compound in accordance with claim 1, (−)-8-chloro-2,3,5,10,11,11a-hexahydro-10-[3-(1-pyrrolidinyl)propionyl]-1H-pyrrolo[2,1-c][1,4]benzodiazepine.

7. The compound in accordance with claim 1, (−)-8-chloro-2,3,5,10,11,11a-hexahydro-10-(3-piperidinopropionyl)-1H-pyrrolo[2,1-c][1,4]benzodiazepine.

8. The compound in accordance with claim 1, (−)-2,3,5,10,11,11a-hexahydro-7-methyl-10-[3-(1-pyrrolidinyl)propionyl]-1H-pyrrolo[2,1-c][1,4-benzodiazepine.

9. The compound in accordance with claim 1, (−)-7,9-dichloro-2,3,5,10,11,11a-hexahydro-10-[3-(1-pyrrolidinyl)propionyl]-1H-pyrrolo[2,1-c][1,4]benzodiazepine.

10. A method of treating anxiety in a warm-blooded animal which comprises administering to said warm-blooded animal an anti-anxiety amount of a racemic benzodiazepine or an optical isomer thereof of the formula:

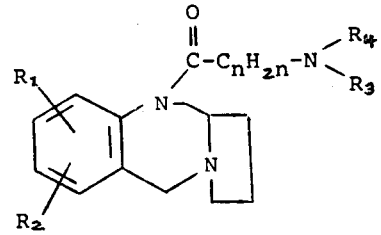

wherein $R_1$ and $R_2$ are selected from the group consisting of hydrogen, lower alkyl, halogen, nitro, amino, diloweralkylamino, trifluoromethyl, lower alkoxy, lower carboxylic acyloxy, benzyloxy and hydroxy and $R_1$ and $R_2$ taken together on adjacent carbons may be methylenedioxy; $R_3$ and $R_4$ are selected from the group consisting of hydrogen, lower alkyl, allyl, propargyl, $C_3$–$C_6$ cycloalkylmethyl and benzyl and $NR_3R_4$ taken together may be pyrrolidinyl, piperidino, 4-methylpiperidino, hexamethyleneimino, morpholino, 1-piperazinyl, 4-methyl-1-piperazinyl or 4-phenyl-1-piperazinyl and $n$ is 1–4.

11. A method in accordance with claim 10 wherein $R_1$ is chloro, $R_2$ is hydrogen, $NR_3R_4$ is pyrrolidinyl and $n$ is 2.

* * * * *